United States Patent [19]

Madaus et al.

[11] 4,162,255

[45] Jul. 24, 1979

[54] PROCESS FOR EXTRACTING ARISTOLOCHIC ACIDS

[75] Inventors: Rolf Madaus, Köln-Brück; Klaus Görler, Bensberg-Refrath, both of Fed. Rep. of Germany

[73] Assignee: Dr. Madaus & Co., Cologne, Fed. Rep. of Germany

[21] Appl. No.: 843,004

[22] Filed: Oct. 17, 1977

[30] Foreign Application Priority Data

Oct. 15, 1976 [DE] Fed. Rep. of Germany ....... 2646545

[51] Int. Cl.$^2$ ........................................... C07D 317/44
[52] U.S. Cl. ............................................. 260/340.5 R
[58] Field of Search ................................. 260/340.5 R

[56] References Cited
FOREIGN PATENT DOCUMENTS 1186980  6/1963  Fed. Rep. of Germany .... 260/340.5 R
7127834  2/1968  Japan ................................. 260/340.5 R

OTHER PUBLICATIONS

Ruecker et al., Planta Medica, vol. 27, No. 1, (1975).

*Primary Examiner*—Ethel G. Love
*Attorney, Agent, or Firm*—Sprung, Felfe, Horn, Lynch & Kramer

[57] ABSTRACT

Aristolochic acids are obtained from aristolochic plant species by alkaline extraction, comprising:
(a) extracting the aristolochic plant species in slightly alkaline medium;
(b) acidifying the extract;
(c) dissolving the precipitate in an organic solvent immiscible with water;
(d) extracting the obtained solution with aqueous alkali;
(e) acidifying the extract; and
(f) separating and optionally recrystallizing the precipitated product.

17 Claims, 1 Drawing Figure

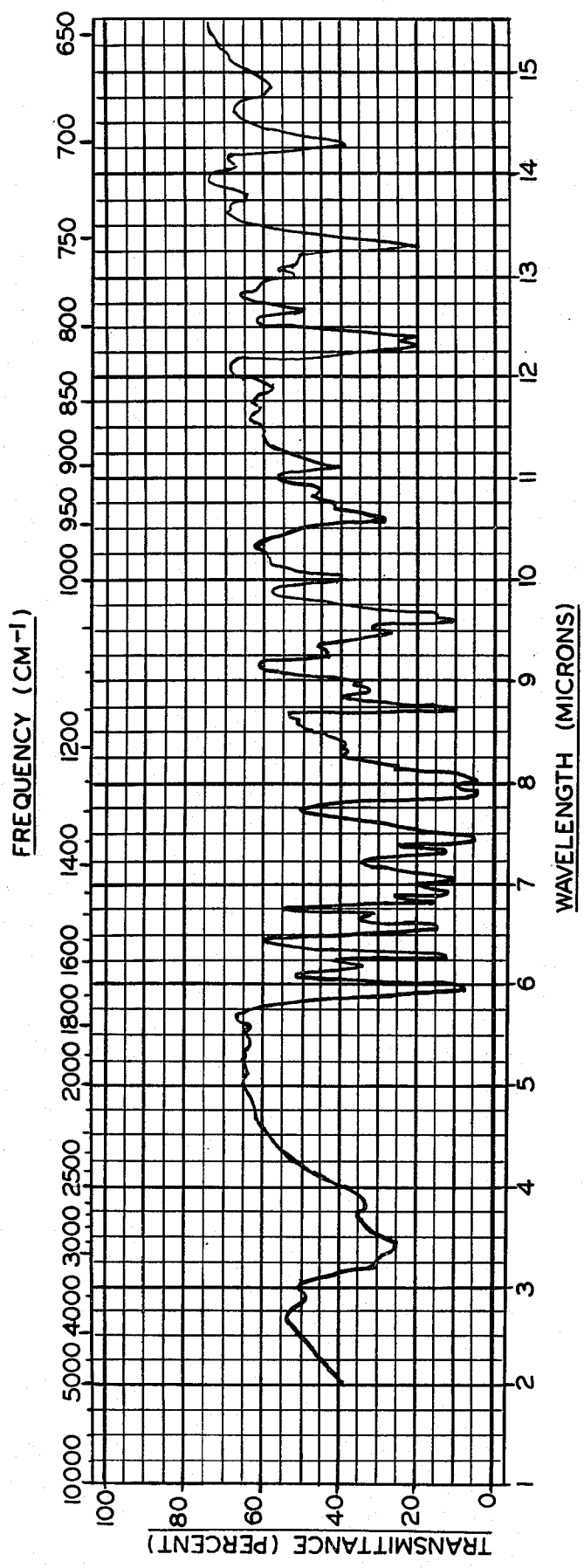

PROCESS FOR EXTRACTING ARISTOLOCHIC ACIDS

The invention relates to a process for obtaining aristolochic acids; more specifically, to a process for obtaining such acids from aristolochic plant species by extraction.

Aristolochic acids are natural substances in plants and are characterized by having a nitro group on a phenathrene core. They exist as a mixture of nitrophenanthrene carboxylic acids in numerous kinds of the *aristolochiaceae*; the acids appearing in *aristolochia clematitis* (L) have been extensively identified as to their chemical structure.

The aristolochic acids are very interesting pharmacologically and are valuable medicaments for many applications, e.g., to impede tumor growth and to stimulate phagocytosis. Thus, there has been a great demand for such acids and a need for an efficient extraction process.

For obtaining larger quantities of aristolochic acids, *aristolochia clematitis (L) is generally used as a starting material; especially the root of this species which has a high content of aristolochic acid.* The roots contain about 5 to 6 times the quantity of acids as the leaves or other parts of the plant. While the content is subject to strong seasonal deviations, a good commercial plant may contain up to 0.6% of aristolochic acids.

The aristolochic acids having the structures I and II below form the main part of the mixture of aristolochic acids.

The aristolochic acid I is a 3,4-methylenedihydroxy-8-methoxy-10-nitrophenanthrene-1-carboxylic acid.

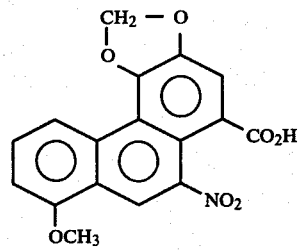

The aristolochic acid II differs from the aristolochic acid I in that it has no methoxy group. It is 3,4-methylenedihydroxy-10-nitrophenanthrene-1-carboxylic acid of the formula:

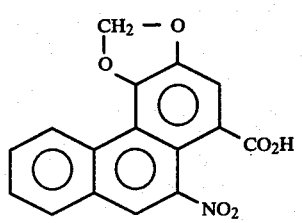

The prior art teaches various procedures for isolating the active substance from the plant. According to W. Schunack et al, Pharmazie 20, pages 685–588 (1965) *Radix aristolochia longae* is first extracted with petroleum ether, and is then treated with ethanol or a less polar solvent (i.e., benzene, methylene chloride), acidic extraction with methylene chloride/diluted sulfuric acid, or methylene chloride/formic acid, being described as especially advantageous. The extract obtained is shaken with 2% caustic soda and then acidified with diluted sulfuric acid. This process has considerable disadvantages since it depends very much on the quality of the plant used as the starting material, and leads sometimes to greasy products.

In the Japanese patent publication 27834/71, there is described a process for extraction of *aristolochia debilis*. According to this disclosure, an extract with ammoniacal water is produced from the plant. This extract is subjected to column chromatography, the elution agent consisting mainly of chloroform and additions of butanol and acetic acid, the product fraction is separated, and the product is isolated from the fraction.

This process and other involving extraction of the plant with aqueous caustic soda is disadvantageous because of the rapid swelling of the plant. The genuine acids are not separated quickly enough (in the form of their salts) and remain too long in alkaline medium in which they are subject to decomposition as already described by Pailer.

According to German Patent Publication Dt-AS 1 186 980, *Radix aristolochiae* is extracted with chloroform, methylene chloride or ether; from the thus obtained solution, the aristolochic acids are extracted as their salts by shaking with an alkaline aqueous solution, the product is precipitated again by acidifying, and, if necessary, is recrystallized. This process has the disadvantage that it depends highly on the grade of drying and the condition of the plant used. As a rule, one obtains greasy substance mixtures saturated with decomposition products.

According to German Patent Publication Dt-AS 1 768 090, *Radix aristolochiae* is extracted at moderate temperatures with a water-miscible alcohol or ketone containing 40 to 60% water, the hot solution obtained containing water is subjected to suction, is then cooled, and the solution is mixed with 3 to 5% dimethyl formamide, and acidified with a mineral acid to a pH-value of 2–3; the aristolochic acids are then allowed to stand, and are thus brought to crystallization. It is, however, disadvantageous to work with mixtures of water and organic water-miscible solvents because the organic solvents are substantially lost. Furthermore, the conditions of precipitation and crystallization are very precarious because of appearance again of decompsotion products, especially at too strong acidic pH-value.

There has thus been a need for a new process for isolating aristolochic acids from *aristolochia* species, which is free of the disadvantages of those processes of prior art, and which leads to an especially product in higher yield in a simple manner.

The invention satisfies this need and provides a process for yielding *aristolochic* acids by following a sequence of steps:

(a) slightly alkaline extraction of the plant
(b) acidifying the extract
(c) dissolving the precipitate in an organic solvent inmiscible with water
(d) extracting the obtained solution with aqueous alkali
(e) acidifying the extract, and
(f) separating the precipitated product, and recrystalizing it if needed.

A preferred way of executing the process according to the invention is:

(a) extracting the plant at a pH-value of 8–8.5 with an aqueous-alkaline, preferably an aqueous solution of $Na_2HPO_4 \cdot n\ H_2O$;

(b) acidifying the extract with a mineral acid to a pH of 5–3;

(c) dissolving the precipitate in an ester from an aliphatic carboxylic acid with 1–10 carbon atoms and with an alcohol with 1–10 carbon atoms, and then filtering the solution from insoluble ingredients;

(d) extracting the obtained solution with aqueous alkali;

(e) acidifying the extract with a mineral acid to a pH of 5–3; and (f) recrystallizing the precipitated product from dimethyl formamide, adding a mixture of an alcohol with 1–10 carbon atoms and an ester of a carboxylic acid with 1–10 carbon atoms and of an alcohol also with 1–10 carbon atoms, in a certain mixture ratio, preferably 2:1.

The precipitate of the above-mentioned process step (c) is a mixture of raw acids with a water content of approximately between 60% and 90%, preferably 80%. This raw acid containing water is suspended in an organic solvent, preferably in an ester as described above, of a carboxylic acid with 1–10 carbon atoms, and of an alcohol with 1–10 carbon atoms, stirring intensely, for example, with a turrax. Favorable esters are methylacetate, ethyl acetate, propyl acetate, butyl acetate, and isobutyl acetate, as well as the corresponding formic acid esters, propionic acid esters, butyric acid esters, and valeric acid esters, especially favorable is ethyl acetate.

The precipitate is dissolved in 100 to 200 times the weight of the above-mentioned esters, preferably ethyl acetate, corresponding to the water-containing precipitate. It is especially preferred to use for the solution 150 to 200 times the weight of ethyl acetate corresponding to the precipitate.

As explained above, the plant is preferably extracted three times in a slightly alkaline medium, and is then once washed with water. This alkaline extraction can be made with an aqueous solution of an alkaline reacting substance, preferably in a diluted solution. Alkaline reacting substances are secondary, and tertiary alkali phosphates, alkali hydrogen carbonates and aqueous solutions of ethanolamine and triethanolamine and the like. Especially preferred is a dilute aqueous solution of $Na_2HPO_4 \cdot 2\ H_2O$, e.g., a 0.03 to 0.3 (especially a 0.06) molar solution of this salt. The extraction can also be made with an aqueous solution of sodium bicarbonate, preferably secondary or tertiary sodium phosphate and the like.

In principle, there are aqueous, basic or slightly basic, solutions useful for the primary extraction of the *aristolochic* acids from the *aristolochic* plant roots. In the known processes there arise, however, considerable difficulties during further cleaning and crystallization. Only because of the appropriate selection of the process steps according to the invention it has been possible to overcome these difficulties by avoiding the formation of decomposition products.

For extraction, a finely ground, not ungreased root, can be used as a preliminary ungreasing is superfluous because of extraction in a pH-range of 8–9, preferably 8–8.5, in aqueous medium.

Surprisingly, the extraction conditions of the process according to the invention do not lead to a decarboxylation of the aristolochic acids as it was supposed according to the hitherto existing knowledge about the reaction of aristolochic acids.

The proportion plant: extraction agent is adjusted to about 1:5 to 1:10 (weight by volume). The extraction may be made according to the eddy current principle with continuous feeding and return of the drug under partial removing of the extracted material via partial current to the decanter.

The extraction of the solution described in step (d) can favorably be made in the way of a counter-current extraction.

The extract obtained from the plant in step (a) is acidified with an acid, preferably with a mineral acid, especially preferred a sulfuric acid. The term "mineral acids" as used herein covers all conventional inorganic non-oxidizing acids, e.g., sulfuric acid, phosphoric acid, hydrochloric acid and the like. According to an especially preferred process of carrying out the invention, it is acidified with sulfuric acid to a pH-value of 3–5, preferably pH 4.0–4.5, while stirring. On this occasion, the raw acids fall out as a fine precipitate. They are then further treated as described above.

The acidification in step (e) of the extract obtained in step (d) is favorably effected with a mineral acid, especially sulfuric acid, while stirring strongly. It is advantageous to allow the acidified extract to stand for a while in order to promote the growth of the particles of the cleaned aristolochic acids. The precipitate is then separated by centrifuging or filtering for example, and dried in vacuo while warming up to 70° to 80° C., for example.

This recrystallization is favorably effected by using a mixture of dimethyl formamide and water; it is preferably recrystallized from dimethyl formamide to which a certain quantity of a mixture of a $C_1$–$C_{10}$ alcohol and an ester of a $C_1$–$C_{10}$ carboxylic acid and of a $C_1$–$C_{10}$ alcohol is added in a certain mixture ratio, preferably 2:1. Especially preferred is dimethyl formamide to which a 10–30%, preferably 20% mixture of methanol: ethyl acetate — 2:1 — is added.

The yields of crystallized acids, although they vary strongly depending on the plant material used, are generally between 0.1 and 0.5% of the starting material. The crystallized acids comprise essentially aristolochic acid I and aristolochic acid II in a ratio 2:1, whereby deviations of ± 20% may occur according to the plant.

All species of aristolochia are suitable as material which have a content of aristolochic acids. Thereto belong, for example, *Radix aristolochia longae, aristolochia clematitis, aristolochia debilis, aristolochia contorta, aristolochia kaempfer, aristolochia manschuriensis, aristolochia fangdu, aristolochia westlandi, aristolochia griffithii* and *aristolochia argentina.* Especially preferred is the use of *aristolochia clematitis.*

Compared with the processes of the prior art, the process according to the invention has the advantage that it leads, in a simpler way, to a yield up to 100% of active substance of better quality than obtained with conventional processes.

The invention is illustrated in the following example:

100 g of finely ground plants of *Radix aristolochia clematitis* are extracted three times, over the period of one hour, at the turrax at room temperature with an aqueous solution of secondary sodium phosphate (11.9 g $Na_2HPO_4 \cdot 2\ H_2O$/liter). The first and second extractions are made with 2 liters each of this solution, the third extraction is made with one liter. After the three extractions, the extracts are combined, centrifuged and then washed with 1 liter of water. The extract solutions and the wash water are combined and after settling, adjusted to pH 4 with sulfuric acid while stirring thoroughly. The precipitate is allowed to stand overnight and is then centrifuged. Thereafter, the residue is stirred into 600 ml of ethyl acetate, and is extracted for half an hour at the turrax at room temperature. The ethyl acetate phase is then clarified and extracted in counter-current fashion three times with 300 ml each of a 0.1 n sodium hydroxide solution. The aristolochic acids are precipitated from the combined alkaline solutions by acidifying with sulfuric acid to pH 4. The precipitate is allowed to stand overnight and is centrifuged and dried.

Yield 0.540 g

It is not necessary to readjust the pH-value during the extraction of the drug with the aqueous sodium phosphate solution. After the first and the second extraction, the pH range is between 7 and 7.5, and increased to pH 8 during the third extraction.

The obtained raw acid is recrystallized from N,N-dimethyl formamide to which has been added 20% (based on N,N-dimethyl formamide) of a 2:1 mixture of methanol:ethyl acetate.

Melting range: 273°–280° decomposition

IR spectrum: See FIG. 1 hereof.

It will be understood that the specification and examples are illustrative, but not limitative of the present invention and that other embodiments within the spirit and scope of the invention will suggest themselves to those skilled in the art.

What is claimed is:

1. Process for obtaining aristolochic acids from aristolochic plant species by alkaline extraction, comprising:
   (a) extracting the aristolochic plant species in slightly alkaline medium comprising an aqueous solution of a secondary or tertiary alkali phosphate or an aqueous sodium bicarbonate solution;
   (b) acidifying the extract with a mineral acid to a pH of 5 to 3;
   (c) dissolving the precipitate in an ester of an aliphatic carboxylic acid of 1 to 10 carbon atoms of an alcohol of 1 to 10 carbon atoms, and filtering off insoluble components;
   (d) extracting the obtained solution with aqueous alkali;
   (e) acidifying the extract with a mineral acid to a pH value of 5 to 3; and
   (f) recrystallizing the precipitated aristolochic acids.

2. Process as claimed in claim 1 wherein the precipitated product from step (f) is recrystallized.

3. Process as claimed in claim 1 comprising as step (a), extracting the aristolochic plant species in an aqueous Na$_2$HPO$_4$ solution at a pH value of 8 to 8.5.

4. Process as claimed in claim 1 comprising as step (d), extracting the resulting solution with aqueous sodium hydroxide.

5. Process as claimed in claim 1 comprising as step (e), acidifying the extract with sulfuric acid to a pH value of 5 to 3.

6. Process as claimed in claim 1 comprising as step (f) separating the precipitated product and recrystallizing same from N,N-dimethyl formamide to which has been added a mixture of an alcohol of from 1 to 10 carbon atoms, and a carboxylic acid ester of from 1 to 10 carbon atoms in each of the acid and alcohol moiety thereof.

7. Process as claimed in claim 6 wherein the ratio of said alcohol to said ester is approximately 2:1.

8. Process as claimed in claim 6 wherein a mixture of methanol/ethyl acetate in a ratio of 2:1 is added to said dimethyl formamide in an amount of from 10 to 30% of the total solution.

9. Process as claimed in claim 1 wherein the precipitate of step (c) is dissolved in ethyl acetate.

10. Process as claimed in claim 9 wherein the precipitate is dissolved in 150 to 200 times its weight of ethyl acetate.

11. Process as claimed in claim 1 wherein the extraction of step (a) is carried out at a pH value of 8.0 to 9.0.

12. Process as claimed in claim 11 wherein said extraction is carried out at a pH of 8.5.

13. Process as claimed in claim 2 wherein the recrystallization step is carried out by using a solution comprising about 80% of N,N-dimethyl formamide and about 20% of a mixture of two parts of methanol and one part of ethyl acetate.

14. Process as claimed in claim 1 wherein the acidification steps (b) and (e) are carried out at a pH of 4 to 4.5.

15. Process as claimed in claim 1 wherein, in step (f), recrystallization is effected by using a mixture of dimethyl formamide and water.

16. Process as claimed in claim 1 wherein, in step (f), the aristolochic acid is recrystallized from dimethyl formamide with a mixture of a $C_1$–$C_{10}$ alcohol and an ester of a $C_1$–$C_{10}$ carboxylic acid.

17. Process as claimed in claim 1 wherein the aristolochic plant species is *Radix aristolochia clematitis* and the process is carried out by
   (a) extracting *Radix aristolochia clematitis* with about 0.06 molar aqueous sodium phosphate solution;
   (b) acidifying the resulting extract with diluted sulfuric acid, hydrochloric acid or phosphoric acid to a pH value of about 4.0;
   (c) dissolving the precipitate in ethylacetate and filtering off insoluble components from the extract;
   (d) extracting the obtained solution with 0.1 N aqueous sodium hydroxide solution;
   (e) acidifying the extract with dilute sulfuric acid to a pH value of 4.0; and
   (f) separating the precipitated product and recrystallizing same from a solution of N,N-dimethyl formamide containing, in an amount of 20% based on the N,N-dimethyl formamide used, a mixture of methanol/ethyl acetate (2:1).

* * * * *